United States Patent
Olsen (10) Patent No.: US 10,772,659 B2
(45) Date of Patent: Sep. 15, 2020

(54) DEVICE AND METHOD FOR INTRAOSSEOUS DENTAL ADMINISTRATION

(71) Applicant: DR. BARNEY PARADIGMS, LC, Sandy, UT (US)

(72) Inventor: Barney Todd Olsen, Sandy, UT (US)

(73) Assignee: DR. BARNEY PARADIGMS, LC, Sandy, UT (US)

( * ) Notice: Subject to any disclaimer, the term of this patent is extended or adjusted under 35 U.S.C. 154(b) by 304 days.

(21) Appl. No.: 15/943,962

(22) Filed: Apr. 3, 2018

(65) Prior Publication Data
US 2019/0298407 A1 Oct. 3, 2019

(51) Int. Cl.
*A61B 17/34* (2006.01)
*A61M 19/00* (2006.01)
*A61M 5/32* (2006.01)
*A61C 1/08* (2006.01)

(52) U.S. Cl.
CPC ............... *A61B 17/34* (2013.01); *A61M 5/32* (2013.01); *A61M 19/00* (2013.01); *A61C 1/081* (2013.01)

(58) Field of Classification Search
CPC ............ A61B 17/3472; A61B 17/1673; A61B 17/1637; A61B 5/151; A61B 5/15103; A61B 5/151526; A61B 5/15142; A61M 19/00; A61M 5/32; A61M 2210/0637; A61M 2210/0631; A61M 2202/048; A61C 1/081
See application file for complete search history.

(56) References Cited

U.S. PATENT DOCUMENTS

| 7,811,260 B2 * | 10/2010 | Miller | A61B 17/32002 604/188 |
| 8,142,365 B2 * | 3/2012 | Miller | A61B 10/025 600/566 |
| 2018/0126093 A1 | 5/2018 | Tuttle | |

OTHER PUBLICATIONS

Tuttle Numb Now available at http://tuttlenumbnow.com/ accessed Jul. 6, 2018.
"X-Tip Intraosseous Anesthetic Delivery System" available at http://www.maillefer.com/product/x-tip/ access Jul. 6, 2018.

* cited by examiner

*Primary Examiner* — Bhisma Mehta
*Assistant Examiner* — Rachel T. Smith
(74) *Attorney, Agent, or Firm* — Workman Nydegger (57) ABSTRACT

An intraosseous tack device is configured to puncture alveolar bone or other human or animal bone at a targeted site of the mouth or body to provide an access point for the delivery of local anesthesia or other medicament. The device includes a tack having a head member and an elongate member extending from the head member. The elongate member is inserted into a sleeve, and the sleeve is coupled to a handle. At least a portion of the sleeve is collapsible, so that when a compressive force is applied to the head member of the tack, the sleeve partially collapses to a shorter length, allowing the distal end of the tack to pass out of the opposite end of the sleeve for puncturing the alveolar bone at the targeted site.

20 Claims, 6 Drawing Sheets

DEVICE AND METHOD FOR INTRAOSSEOUS DENTAL ADMINISTRATION

CROSS-REFERENCE TO RELATED APPLICATIONS

N/A.

BACKGROUND

Local anesthetics are used in many dental procedures to prevent patient pain. Often, a topical anesthetic is applied to numb an area in preparation for the administration of a local anesthetic via injection. In some procedures, particularly those involving the maxillary teeth and the anterior mandibular teeth, local anesthetic is administered via buccal infiltration. During buccal infiltration, a needle is inserted into the soft tissue near the bone and the anesthetic is then injected through the needle so as to be in close proximity to the bone. The anesthetic then passes through pores in the outer cortical bone surface until it reaches nerve filaments inside the "spongy" cancellous bone.

Administration of anesthesia through infiltration is only effective where a sufficient amount of anesthesia is able to permeate through the surrounding tissues. For example, infiltration will fail where the local anesthetic is unable to diffuse through the cortical bone. Areas of the mouth where a thick cortical plate exists have limited ability to distribute and diffuse anesthesia into the cancellous bone where it can act on targeted nerves. Typically, the cortical plate is relatively thicker at mandibular teeth than maxillary teeth, and is relatively thicker at more posteriorly located teeth than more anteriorly located teeth. Thus, for some areas of the mouth such as near mandibular molars, infiltration is typically not a viable option for anesthetization.

A similar technique is intraligamentary injection, where the anesthetic is injected into the periodontal ligament(s) of the targeted tooth/teeth. The anesthetic then reaches the pulp via natural perforations in the tooth/teeth. This method, however, is often associated with sharp pain during injection as well as following the procedure. In addition, for posteriorly located teeth, it can be difficult to properly orient the syringe to a workable position for injecting the needle tip into the periodontal ligament.

In circumstances where infiltration and/or intraligamentary injection are not feasible, such as in various procedures involving mandibular molars, for example, a common anesthetization method is the inferior alveolar nerve block ("IANB"). An IANB is carried out by injecting the local anesthesia near the inferior alveolar nerve before it enters the mandibular foramen. Compared to anesthetization via infiltration, an IANB takes longer to take effect, and typically lasts much longer (e.g., on the order of an hour or several hours rather than minutes). Also, diffusion of the anesthesia effects the nearby lingual nerve, which innervates the tongue. After an IANB, a patient will lose sensation in their mandibular teeth (on one side of the mouth where the block was administered), the lower lip and chin, and parts of the tongue and lingual gingival tissue.

Although often effective for their purpose, IANBs have several limitations. In many circumstances an IANB is "overkill" because such a large portion of the mouth is anesthetized even though the actual targeted area needing it is small. Further, because of the time delay before numbing begins, it may be difficult for practitioners to accurately gauge the amount of anesthesia required. In addition, an IANB takes a relatively long time to wear off, and there is a risk of accidental self-inflicted trauma following the procedure. For example, a patient may unknowingly bite and injure the lip or tongue while tissues are still numb, or may inadvertently burn the mouth by drinking a fluid that is too hot.

Another technique is intraosseous administration of anesthesia. In this technique, the anesthesia is deposited directly into the cancellous alveolar bone near the root(s) of the targeted tooth to be anesthetized. To reach the spongy cancellous bone, a small hole must first be made in the outer cortical plate. Typically, this is accomplished using a drill (such as the commercially available "X-Tip" delivery system) or by using a relatively large gauge needle to puncture the cortical plate. Conventional methods of intraosseous delivery are limited by the difficulty of puncturing the cortical bone in certain areas of the mouth, such as near mandibular molars where the cortical plate is particularly thick. In addition, although a mechanical drill may alleviate some of the difficulties in puncturing the cortical bone, it can also cause the build up of heat which can damage surrounding tissues. Also, because the access hole must be made near the root(s) of the targeted tooth, there is an inherent risk that the drill will reach and damage the root(s).

In sum, nerve blocks such as an IANB are limited by their delayed onset, overly broad numbing effect, and overly long duration. More localized methods of anesthesia delivery can avoid some of these limitations, but are not always appropriate or available in particular circumstances and/or for particular teeth. Accordingly, there is a long felt and ongoing need for improved devices and methods for anesthetizing teeth and surrounding tissues.

BRIEF SUMMARY

The present disclosure relates to devices and methods for puncturing alveolar bone or other human or animal bone to provide an access point for intraosseous delivery of a local anesthetic or other medicament. In one embodiment, an intraosseous tack device includes a tack fitted within a sleeve. The tack includes a flattened head member and an elongate member extending from the head member. The sleeve includes a proximal end (i.e., upper end), a distal end (i.e., bottom end), and a lumen extending along a longitudinal axis between the proximal end and the distal end. The lumen is sized to receive the elongate member of the tack. The lumen has a diameter that is smaller than a diameter of the head member of the tack to prevent passage of the head member of the tack into the lumen.

The sleeve includes a rigid portion and a collapsible portion. The collapsible portion is configured to collapse along a line substantially parallel to the longitudinal axis of the sleeve to shorten the sleeve. Preferably, the tack and sleeve are sized such that when the tack is placed within the sleeve and the collapsible portion of the sleeve is in an uncollapsed position, the elongate member is not exposed.

The device may be actuated by a user pressing against the head member of the tack. When a sufficient compressive force is provided, the head member of the tack transfers the compressive force to the collapsible portion of the sleeve and the collapsible portion moves toward the collapsed position, thereby shortening the length of the sleeve. This allows the elongate member of the tack to extend beyond the distal end of the sleeve.

The sleeve and tack may be used without an additional handle. In other embodiments, the device includes a handle. For example, the sleeve may include one or more attachment features, such as a groove or snap connection, configured to engage with corresponding features of a handle. When connected, the handle preferably extends in a direction transverse to the longitudinal/luminal axis of the sleeve (e.g., in a direction orthogonal to the axis of the sleeve). The handle may be selectively attachable to the sleeve or may alternatively be integrally formed with and coupled to the sleeve.

In use, the device is positioned so that the distal end of the sleeve is placed against tissue in a targeted area of a patient's mouth where it is desired to provide an access point for delivering local anesthetic. The user may then apply a compressive force by pressing against the head member of the tack. Upon application of sufficient compressive force, the collapsible portion of the sleeve shortens, allowing the elongate member of the tack to move further distally beyond the distal end of the sleeve. This allows the elongate member of the tack to extend into the alveolar bone at the targeted site. The elongate member penetrates the cortical plate and provides an access point for delivering local anesthetic to the cancellous bone.

BRIEF DESCRIPTION OF THE DRAWINGS

To further clarify the above and other advantages and features of the present disclosure, a more particular description will be rendered by reference to specific embodiments illustrated in the appended drawings. It is appreciated that these drawings depict only illustrated and exemplary embodiments of the disclosure and are therefore not to be considered limiting of its scope. Exemplary embodiments of the disclosure will be described with additional specificity and detail through the use of the accompanying drawings in which.

DETAILED DESCRIPTION

Introduction

Figure 1:
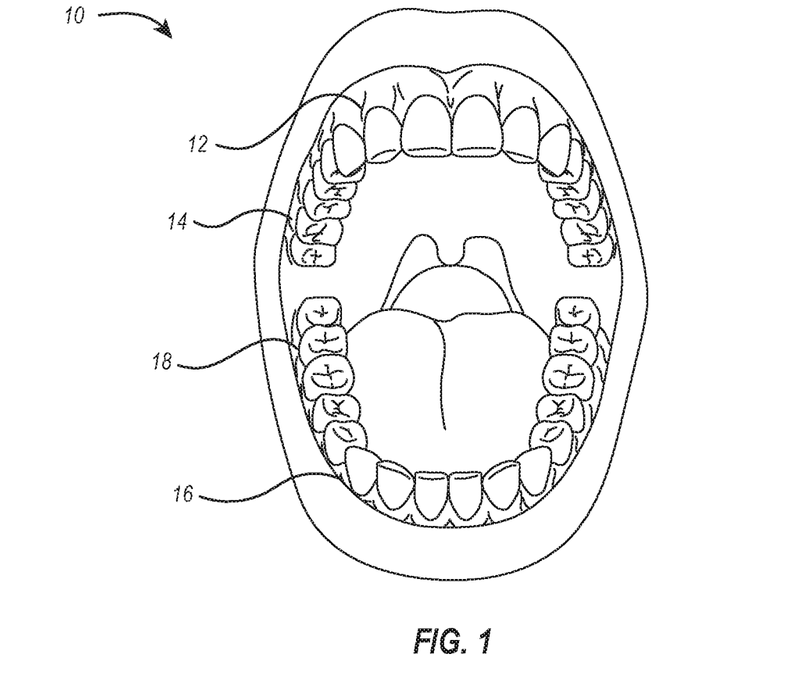
FIG. 1 illustrates a front view of a human mouth showing the maxillary and mandibular teeth at anterior and posterior regions of the mouth.

FIG. 1 illustrates a front view of a human mouth 10 showing the maxillary (upper) and mandibular (lower) teeth. The mouth 10 includes anterior (front) and posterior (rear) regions. The illustrated Figure roughly shows an anterior maxillary region 12, a posterior maxillary region 14, an anterior mandibular region 16, and a posterior mandibular region 18. Generally, the hard, outer cortical plate of the alveolar bone (the bone that contains the tooth sockets) will be thicker in more posterior regions of the mouth compared to more anterior regions of the mouth and is generally thicker in the mandible than in the maxilla. The posterior mandibular region 18 therefore typically has the thickest cortical plate relative to other regions of the mouth 10.

For intraosseous administration of anesthesia, the hard, outer cortical plate of the alveolar bone must be punctured to provide an access point to the softer, spongy cancellous bone proximate the tooth roots. Puncturing the cortical plate is more difficult at regions where the cortical plate has greater thickness, and providing a suitable access point can present a serious technical challenge. Because of the associated challenges with these regions, and because of the ability of the described embodiments to overcome these challenges, the following examples are often described in the context of anesthetizing a posteriorly located mandibular tooth (e.g., a mandibular molar). It will be understood, however, that the components and features described herein may also be utilized for providing an access point for administering anesthesia in any other desired region of the mouth, including near maxillary teeth and/or near more anteriorly located teeth. Further, certain embodiments may be utilized outside of the dental/orthodontal field. For example, an intraosseous device as described herein may be used to quickly provide an access site for the intraosseous delivery of a medicament (e.g., anesthetic, epinephrine, or other medical composition) within other bones of a patient (e.g., limb bones such as the tibia).

Figure 2:
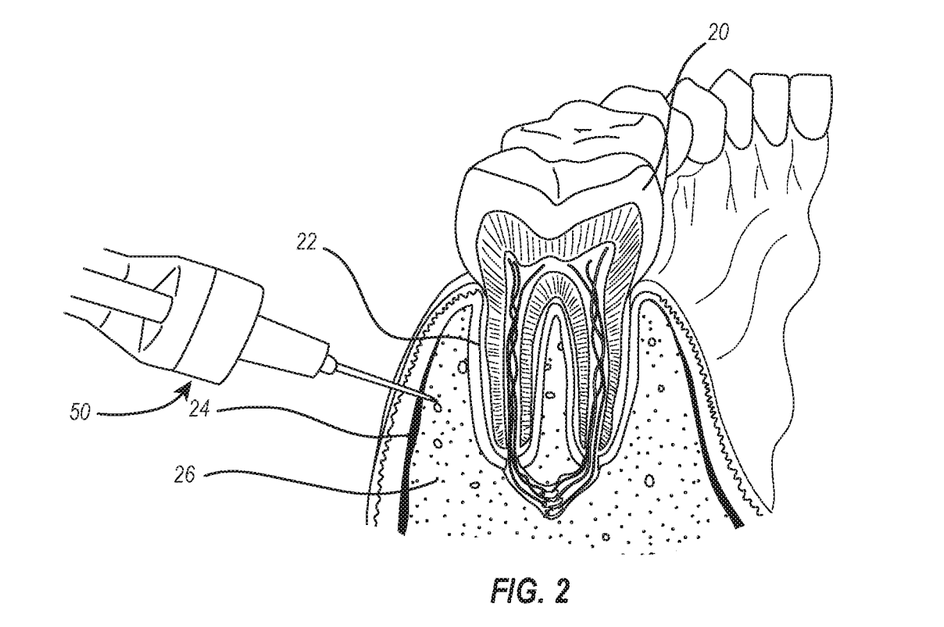
FIG. 2 illustrates a cross-sectional view of a mandibular molar showing intraosseous delivery of anesthesia.

FIG. 2 illustrates a cross-section of a mandibular molar 20 within its corresponding tooth socket. The cross-sectional view illustrates the hard, outer cortical plate 24 and the spongy, inner cancellous bone 26. During intraosseous administration of anesthesia, the tip of the needle 50 must be positioned past the cortical plate 24 and within the cancellous bone 26, as shown. FIG. 2 also illustrates the periodontal ligament 22 which is disposed between the tooth 20 and the bone of the socket and which functions to attach the tooth 20 to the socket.

Figure 3:
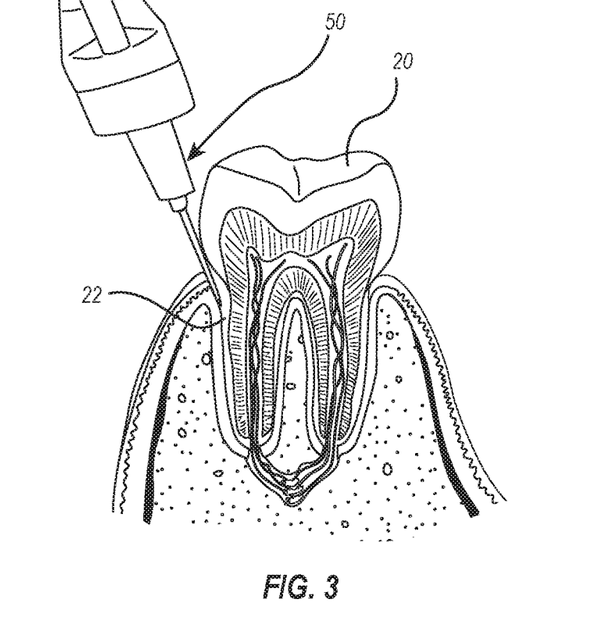
FIG. 3 illustrates a cross-sectional view of a mandibular molar showing intraligamentary injection of anesthesia.

FIG. 3 illustrates placement of a needle 50 into the periodontal ligament 22 as part of an intraligamentary anesthesia delivery procedure. Although this type of administration can be effective, it is often associated with sharp pain during injection and additional pain following the procedure. In many circumstances, an intraosseous administration route is preferable. However, puncturing the cortical plate to form a suitable access point can be challenging.

Figure 4:
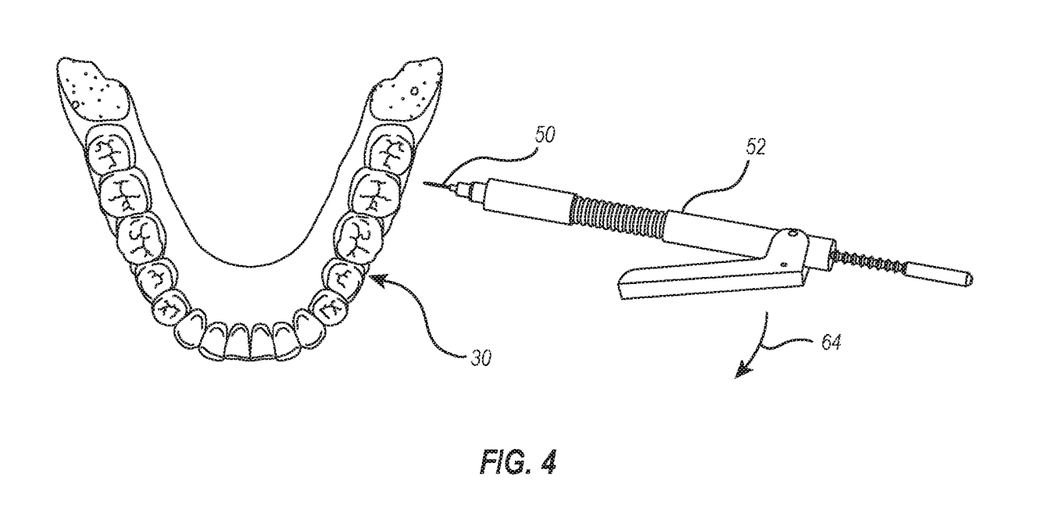
FIG. 4 illustrates the mandible from a superior perspective, showing a desired or required orientation of a syringe (this type of syringe sold under the trade name "Ligajet") during attempted anesthetization of a mandibular molar.

Further, as schematically illustrated in FIG. 4, during anesthetization of a posterior tooth it can be difficult to orient the syringe 52 and needle 50 in a desired position orthogonal to the buccal surface of the mouth 30. The orthogonal position of the syringe 52 and needle 50 shown in FIG. 4 will in practice be difficult to achieve or maintain because a patient's cheeks will push against the syringe 52 and will tend to rotate the syringe 52 away from the orthogonal position, as shown by arrow 64. This can make it difficult to properly orient the needle 50 with respect to the periodontal ligament 22 (when attempting intraligamentary delivery) or with respect to the buccal surface of the gingivae (when attempting intraosseous delivery)

Figure 5:
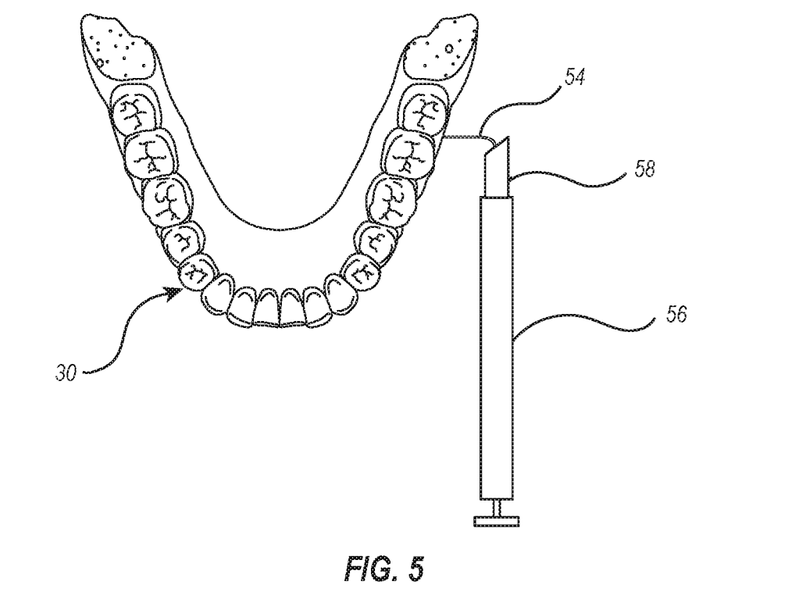
FIG. 5 illustrates the mandible from a superior perspective, showing a bent-needle syringe device during an attempted anesthetization of a mandibular molar.

FIG. 5 illustrates a "bent-needle" syringe configuration that may be utilized in an intraosseous anesthetic procedure. One example of such a device is the commercially available "TuttleNumbNow" device. As shown, the needle 54 is bent to a 90-degree angle relative to the syringe 56 so that the needle 54 may be orthogonally positioned relative to the targeted buccal surface. The device also includes a sheath 58 intended define the curve formed in the needle 54 during bending and to provide a surface for the user to push against when attempting to puncture the bone. If puncture is successful, the user may then deliver the local anesthetic by actuating the syringe 56.

Figure 6:
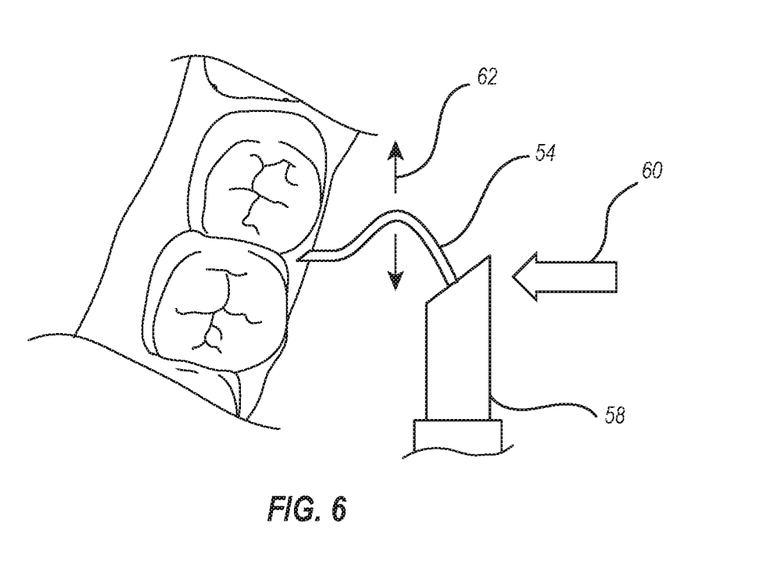
FIG. 6 is an expanded view of the bent-needle syringe device of FIG. 5, showing potential needle bending that may occur during the attempted anesthetization.

Such devices have several limitations, however. As shown in FIG. 6, when a force (shown by arrow 60) is directed against the sheath 58, the needle 54 will be contacted against the targeted cortical plate. In some circumstances, it will be difficult to puncture the cortical plate with the needle 54, and the needle 54 may bend or even break before puncturing through the bone, as shown by arrows 62. Further, the needle 54 must inherently include a hollow inner lumen to enable delivery of the anesthetic. This required structural feature necessarily limits the needle's resistance to bending relative to a solid structure of otherwise similar size, shape, and construction. Moreover, even if puncturing through the cortical plate using a needle is successful, the method carries the risk that the needle will become clogged with portions of the tissue it passes through, preventing delivery of anesthesia to the cancellous bone using the needle once the needle tip has reached the target.

Intraosseous Tack Device

Figure 7:
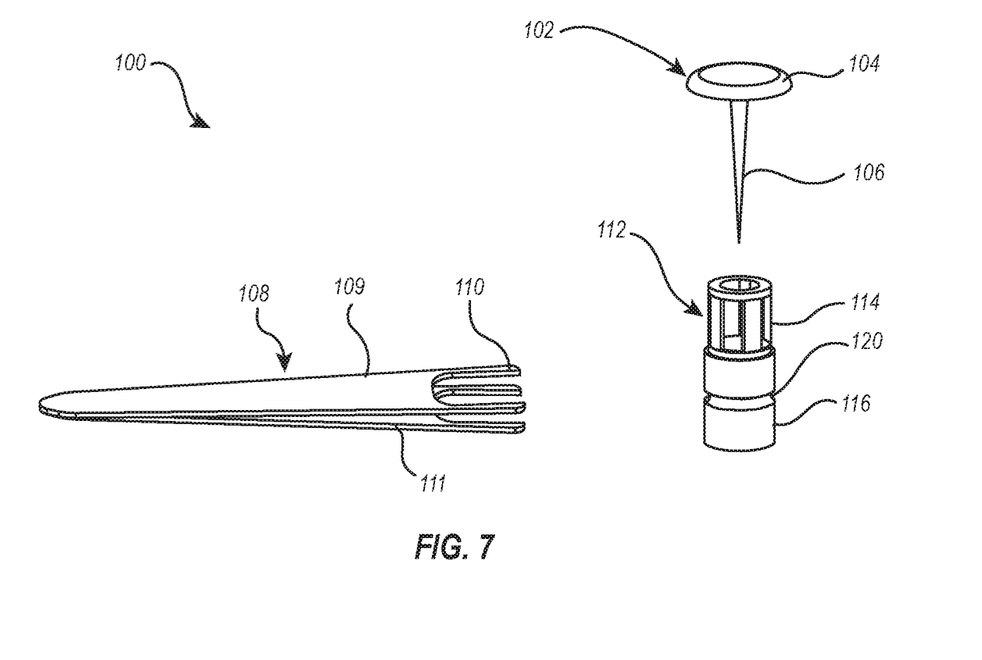
FIG. 7 illustrates an exploded view of an exemplary intraosseous tack device configured for puncturing the cortical plate of a targeted area of the mouth to provide an access point for intraosseous delivery of anesthetic.
Figure 8:
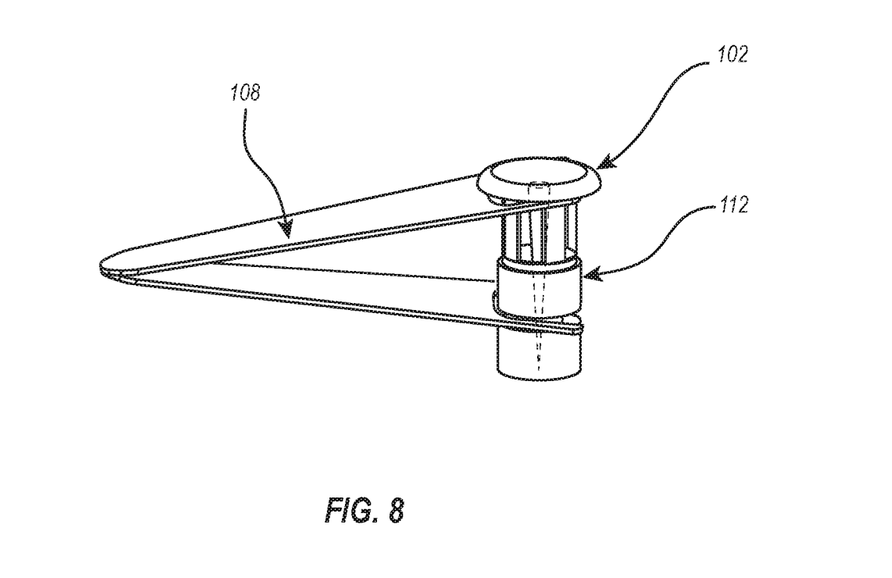
FIG. 8 illustrates the intraosseous tack device of FIG. 7 in an exemplary assembled form.

FIG. 7 illustrates an exploded view of an exemplary intraosseous device 100, and FIG. 8 illustrates an assembled view of the device 100. The device 100 includes a tack 102, a sleeve 112, and a handle 108. The tack 102 includes a flattened head member 104 and an elongate member 106 extending from the head member 104. Preferably, the elongate member 106 is not a needle and does not have a hollow lumen/interior. Rather, the elongate member 106 is preferably solid (i.e., with a solid cross section).

A solid elongate member 106 provides several benefits. Compared to a hollow needle of similar size, shape, and construction, the solid elongate member 106 has greater resistance to bending and breakage when an axial force is applied in an attempt to penetrate the alveolar bone. In addition, because the elongate member 106 is solid, problems associated with tissues clogging the lumen of the device are avoided. Rather, the solid elongate member 106 is capable of effectively providing a clean access point through the cortical plate and into the cancellous bone.

The head member 104 of the tack 102 is shown here with a flattened, circular shape. Other embodiments may include tacks with other shape features. For example, some embodiments may include a tack with a head member that is polygonal (e.g., triangular, square, etc.), rounded, bubble-shaped, cylindrically-shaped, or otherwise shaped. The head member 104 may have a frictional feature or pattern to improve tactile grip during use.

Regardless of the exact shape of the head member 104, it is preferred that the head member 104 have a diameter that is larger than an inner diameter (i.e., lumen diameter) of the sleeve 112. This prevents the head member 104 from passing into the lumen of the sleeve 112 and defines the positional limit between the tack 102 and the sleeve 112. The head member 104 of the tack 102 may have a diameter that is larger than an inside diameter of the sleeve 112 by a factor of about 1.25 to about 10, or more preferably by a factor of about 1.5 to about 10. Diameter ranges within the foregoing ranges provide effective operability of the device by balancing size constraints for fitting the tack 102 within the sleeve 112 with overall size constraints of the device (which must be usable within the mouth) and with the need to have a tactile, actuatable surface by way of the head member 104.

As used herein, the "diameter" of a component refers to the longest dimension across the component from one side to the other, whether or not the component is circular or spherical. For example, the "diameter" of a square-shaped component may be measured diagonally from one corner to the opposite corner.

The elongate member 106 is sized so as to fit within the lumen of the sleeve 112. Preferably, the lumen of the sleeve 112 is sized to receive the elongate member 106 with a tight tolerance to minimize the amount of lateral movement or "play" of the elongate member 106 within the sleeve 112. The illustrated embodiment shows the elongate member 106 with a tapering profile. Alternatively, the cross-sectional diameter of the elongate member 106 may be substantially constant along its length. For example, some embodiments may include a cross-sectional diameter that is substantially constant for most of the length of the elongate member (e.g., 70-99% of its length), but with a distal tip that is tapered or beveled to form a finer/sharper point.

The size of the elongate member 106 is an important consideration in design of the device 100. For example, an overly large diameter may leave an overly large puncture in the patient's alveolar tissue and may cause undue pain and/or extended healing times. However, an overly small diameter may be unable to effectively puncture the targeted bone. In this regard, for the given puncturing forces required, the solid construction of the elongate member 106 beneficially enables use a smaller diameter as compared to a needle. In presently preferred embodiments, an elongate member 106 having a diameter of about 0.2 mm to about 0.7 mm (e.g., about 0.3 mm, 0.4 mm, 0.5 mm, 0.6 mm) appears to provide effective results for a typical application, with a particularly preferred diameter size ranging from about 0.3 mm to about 0.5 mm (corresponding approximately to needle gauge sizes of 25 to 30). Other particular patient, procedure, or application needs may suggest or require the use of other sizes, however.

In the illustrated embodiment, the sleeve 112 includes a collapsible portion 114 and a rigid portion 116. As explained in greater detail below, the collapsible portion 114 is configured to collapse and shorten along the longitudinal axis of the sleeve 112 when the sleeve 112 is exposed to an axially-directed compressive force. Typically, this compressive force will be provided by a user's thumb and/or finger. The compressibility of the collapsible portion 114 allows the sleeve 112 to be effectively shortened and allows the elongate member 106 of the tack 102 to translate further through the lumen of the sleeve 112. The rigid portion 116 provides greater axial rigidity and is configured to resist collapsing when exposed to the compressive force.

As used herein, the proximal or "upper" end of the sleeve refers to the end adjacent to the head member 104 of the tack 102 when the device is assembled. The distal or "lower" end of sleeve refers to the opposite end through which the distal, puncturing end of the elongate member 106 will pass when the device is actuated. The illustrated embodiment positions the collapsible portion 114 adjacent the upper end of the sleeve 112 and the rigid portion adjacent the lower end of the sleeve 112. Other embodiments may reverse the relative positions such that the collapsible portion is adjacent the lower end and the rigid portion is adjacent the upper end. In such an embodiment, the head member of the tack would be adjacent to the rigid portion and the distal end of the elongate member would extend out of and beyond the collapsible portion when the device was actuated.

The rigid portion 116 of the illustrated sleeve embodiment also includes an attachment feature 120 adapted to enable the handle 108 to couple to the sleeve 112. As shown, the attachment feature 120 may be a groove, notch, or similar structure shaped to engage with a corresponding attachment feature 110 of the handle 108. Other embodiments may additionally or alternatively include other attachment features, such as threaded connections, magnetic connections, clasps, snap-fit connections, and combinations thereof.

In the illustrated embodiment, the handle 108 is selectively detachable from the sleeve 112. This allows, for example, the handle 108 to be sterilized and reused while the sleeve 112 and tack 102 are disposed of after use on a particular patient. In alternative embodiments, the handle 108 may be permanently coupled to the sleeve 112 as part of an integrated handle/sleeve unit. The handle 108 is shown here as having a plier-like construction with two opposing prongs or members 109 and 111. In other embodiments, the handle 108 may be constructed in an alternative form, such as a simple rod construction, an ergonomic handle construction, a band-shaped construction, or other shape suitable for holding by a user.

The opposing members 109 and 111 may be biased toward an open position such that there is space between the ends of each member 109 and 111 near the attachment feature 110. For example, the handle 108 may be biased toward the open position shown in FIG. 8. From the position shown in FIG. 8, the device may be actuated to the position shown in FIG. 9 by applying a compressive force to the head member 104 sufficient to overcome the bias in the handle 108 and/or the collapsible portion 114. After the device has been actuated to the position shown in FIG. 9 and the compressive actuating force has been removed, the bias of the handle 108 and/or collapsible portion 114 toward their default positions will cause the device to automatically return to the non-actuated position shown in FIG. 8.

In some embodiments, the head member 104 of the tack 102 is attached to the sleeve 112. In the illustrated embodiment, for example, a bottom surface of the head member 104 may be attached to the top of the collapsible portion 114 of the sleeve 112. The attachment may be achieved using an adhesive or other suitable attachment means. Attaching the head member 104 to the sleeve 112 can beneficially prevent the tack 102 from detaching and falling away from the sleeve 112. To maintain proper functionality of the device, however, the elongate member 106 should still be longitudinally translatable within the lumen of the sleeve 112.

As best seen in FIG. 8, the elongate member 106 of the tack 102 has a length that is no longer than the length of the sleeve 112 when the collapsible portion 114 is in an uncollapsed position. This prevents the distal end of the tack 102 from extending beyond the bottom of the sleeve 112. In other words, when the device is assembled and the tack 102 is properly positioned within the sleeve 112, the puncturing end of the elongate member 106 should not be immediately accessible. This prevents accidental sticks since the sharp, puncturing end of the elongate member 106 will only be exposed when a compressive force is properly applied to actuate the device.

Figure 9:
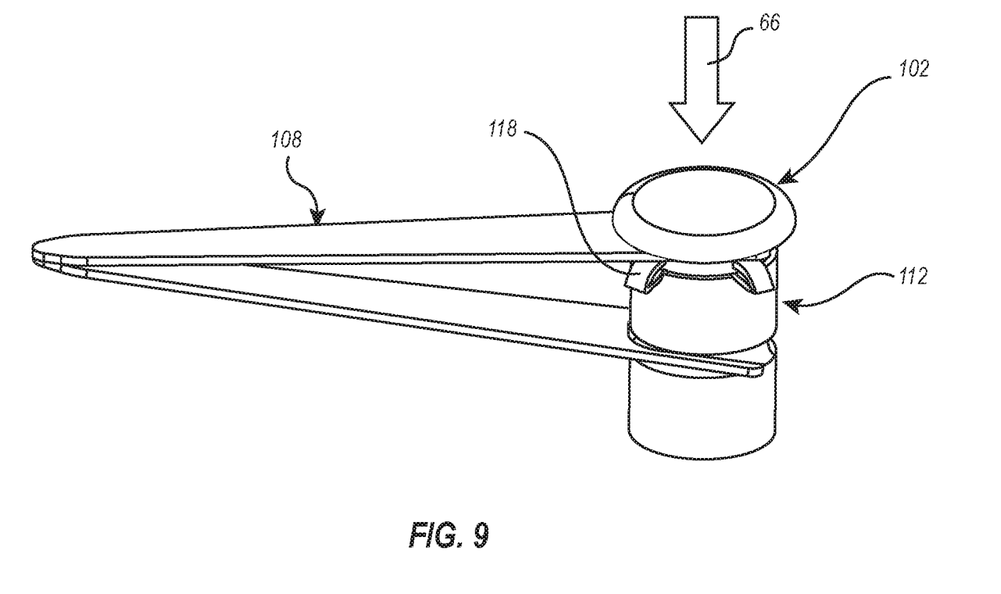
FIG. 9 illustrates actuation of the intraosseous tack device of FIGS. 7 and 8.

FIG. 9 illustrates actuation of the intraosseous device 100. When a compressive force (as shown by arrow 66) is applied to the head member of the tack 102, the collapsible portion of the sleeve 112 moves to a collapsed position, as shown. This allows the distal end of the tack 102 to pass out of the bottom end of the sleeve 112. In use, the bottom end of the sleeve 112 may be placed against targeted tissue where it is desired to puncture the bone and provide an anesthesia access point. The user then actuates the device by pressing on the head member of the tack 102 to cause the collapsible portion of the sleeve 112 to collapse and to allow the elongate member of the tack 102 to pass out of the sleeve to puncture bone at the targeted position.

The elongate member 106 preferably has a length such that, when the device is actuated, the elongate member 106 extends beyond the bottom end of the sleeve 112 a distance of about 1 mm to about 6 mm, or more preferably about 2 mm to about 5 mm. In other words, the elongate member 106 preferably has a length that is about 1 mm to about 6 mm, or about 2 mm to about 5 mm greater than a length of the sleeve when the sleeve is in a collapsed position.

For a typical application, a puncture depth within these ranges provides for an effective access point for administering anesthesia. In particular, the depth should be sufficient to provide good access to the cancellous bone in the targeted area, and should be deep enough to allow the anesthesia to diffuse effectively to surrounding tooth tissue once administered. At the same time, an overly deep penetration can injure more tissue than is needed for effective anesthetization. Lengths within the foregoing ranges therefore balance the need to provide effective penetration with the desire to avoid unnecessary injury risks and unnecessary use of materials. Other particular patient, procedure, or application needs may suggest or require the use of other lengths, however.

As shown in FIG. 9, the collapsible portion of the sleeve 112 includes a plurality of separable sections 118 configured to separate from one another to allow the collapsible portion to expand radially when compressed. This allows the overall length of the sleeve 112 to shorten, and thus allows the distal end of the tack 102 to pass out of the bottom end of the sleeve 112. As shown, the separable sections 118 may be oriented longitudinally (i.e., substantially parallel with the luminal axis of the sleeve 112). Other embodiments may include one or more separable sections oriented non-longitudinally. Other embodiments may additionally or alternatively include collapsible portions that include springs, accordion tubes, tube with sufficient columnar elasticity, other collapsible and/or resilient mechanisms, and combinations thereof.

In some embodiments, the collapsible portion 114 is resiliently biased toward the uncollapsed position. For example, when the device is actuated, the collapsible portion 114 is moved to the collapsed position upon application of a sufficient compressive force. When the compressive force is removed, the collapsible portion 114 returns to the uncollapsed position. In use, such a feature allows the exposed, puncturing end of the tack 102 to be drawn back within the sleeve 112 after the puncture has been made. This can beneficially prevent accidental sticks to the patient or user while withdrawing and handling the device following puncture formation.

Figure 10:
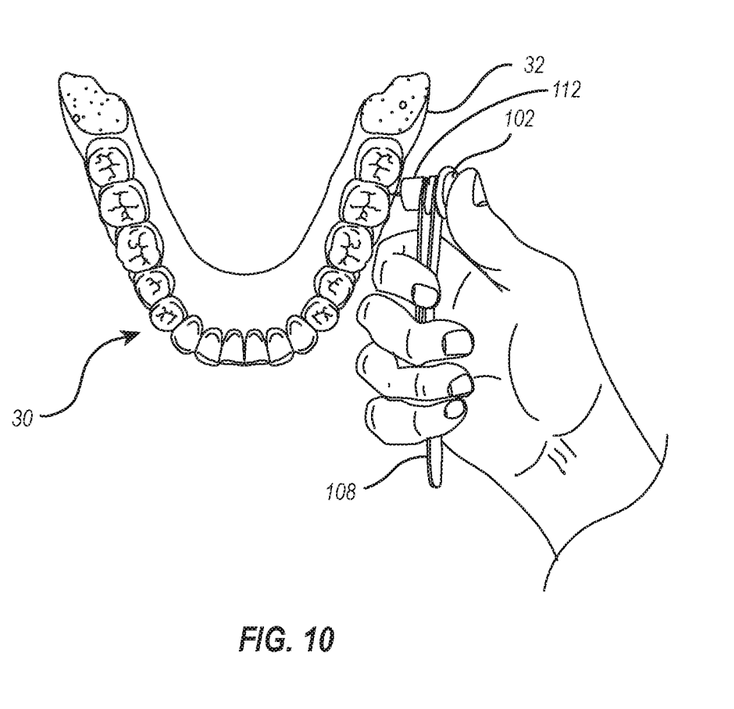
FIGS. 10 and 11 illustrate exemplary methods of gripping, positioning, and actuating the intraosseous tack device in order to form an access point for intraosseous delivery of anesthetic near a targeted molar.
Figure 11:
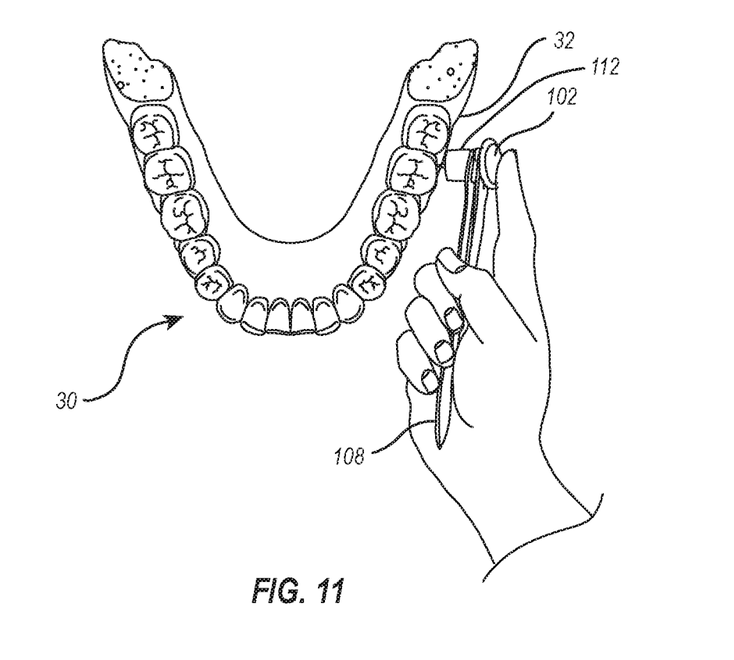

FIGS. 10 and 11 schematically show exemplary uses of the intraosseous device 100. As shown, a user may grip the handle 108 and position the device near the targeted tissue to be punctured. Unlike a typical syringe, the handle 108 does not need to be orthogonal to the buccal surface 32, and may beneficially be aligned with the buccal surface 32 for easier access to posterior regions of the mouth 30. The sleeve 112 and tack 102 are positioned such that the luminal axis is orthogonal to the buccal surface 32. Typically, prior to puncture of the soft tissue and bone at the targeted site, the user administers topical and local anesthetic. For example, the user may first apply a topical anesthetic to the outer surface of the gingival tissue at and near the targeted site, and then may use a syringe to apply an amount of local anesthetic within the gingival tissue before proceeding with the intraosseous technique.

As described above, the user contacts the bottom surface of the sleeve 112 against the gingivae near the targeted tooth/teeth to be numbed (typically between two teeth), and then presses the tack 102 to push it through the sleeve 112, puncture the cortical plate, and provide an access point for delivering anesthesia. As shown, the device may be held in any desirable or preferred manner, such as with a thumb-actuating grip (FIG. 10) or a finger-actuating grip (FIG. 11). Following formation of the access point, the local anesthesia may be easily delivered using standard syringe and needle components. The needle may be bent to an angle for easier positioning at the access point, if desired. Because an access point has already been formed, the problems associated with using a needle to puncture bone (e.g., breakage, clogging) are avoided.

Because of the manual manner in which the device is actuated, it also beneficially provides effective tactile feedback to the user. In contrast, a user may accidentally reach and damage tooth roots when using a mechanized mechanism such as a mechanized drill. When using the disclosed device, the user is able to receive tactile feedback indicating how the procedure is advancing. For example, a user will typically be able to feel resistance as the tack is pressed against the cortical bone and will feel the "give" as it passes the cortical bone and enters the cancellous bone. Further if the tack happens to approach a root during penetration, the user will be able to feel the contact and will thus know to limit further penetration.

The illustrated device may be constructed using a variety of different suitable materials, such as medical-grade polymers, metals, and/or ceramics. In one embodiment, the sleeve 112 is constructed of a polymer and the tack 102 and handle 108 are constructed of stainless steel. Other suitable material combinations may be utilized, however.

The invention claimed is:

1. A device configured for puncturing bone to provide an access point for intraosseous delivery of a medicament, the device comprising:
a tack having a flattened head member and an elongate member extending from the head member; and
a sleeve having a proximal end, a distal end, and a lumen extending along a longitudinal axis between the proximal end and the distal end, the lumen being sized so as to receive the elongate member of the tack and being sized so as to prevent passage of the head member of the tack into the lumen,
wherein the sleeve includes a rigid portion and a collapsible portion, the collapsible portion being configured to collapse along a line substantially parallel to the longitudinal axis of the sleeve to thereby shorten the sleeve.

2. The device of claim 1, wherein the sleeve further comprises an attachment feature adapted to enable a handle to couple to the sleeve.

3. The device of claim 2, wherein the attachment feature is disposed at the rigid portion of the sleeve.

4. The device of claim 3, wherein the attachment feature includes a groove disposed within the rigid portion of the sleeve.

5. The device of claim 1, wherein the head member of the tack has a diameter that is larger than an inside diameter of the sleeve by a factor of about 1.25 to 5.

6. The device of claim 1, wherein the elongate member of the tack includes a sharpened distal tip.

7. The device of claim 1, wherein the elongate member of the tack has a diameter of about 0.1 mm to about 0.9 mm.

8. The device of claim 1, wherein the elongate member of the tack has a diameter of about 0.3 mm to 0.5 mm.

9. The device of claim 1, wherein the collapsible portion of the sleeve is configured to expand radially outward to allow shortening of the sleeve upon exposure to a sufficient compressive force.

10. The device of claim 9, wherein the collapsible portion includes a plurality of separable sections configured to expand radially outward upon exposure to the sufficient compressive force.

11. The device of claim 10, wherein the plurality of separable sections are oriented longitudinally.

12. The device of claim 1, wherein the head member of the tack is connected to the sleeve.

13. The device of claim 12, wherein the head member of the tack is connected to the collapsible portion of the sleeve.

14. The device of claim 1, wherein the elongate member of the tack has a length that is no longer than a length of the sleeve when the sleeve is in an uncollapsed position.

15. The device of claim 14, wherein the elongate member of the tack has a length that is about 1 mm to about 6 mm greater than the length of the sleeve when the sleeve is in a collapsed position.

16. The device of claim 1, wherein the collapsible portion is configured to move to a collapsed position upon application of a sufficient compressive force and wherein the collapsible portion is biased toward an uncollapsed position such that it returns to the uncollapsed position upon removal of the compressive force.

17. A device configured for puncturing bone to provide an access point for intraosseous delivery of a medicament, the device comprising:
a tack having a flattened head member and an elongate member extending from the head member;
a sleeve having a proximal end, a distal end, and a lumen extending along a longitudinal axis between the proximal end and the distal end, the lumen being sized so as to receive the elongate member of the tack and being sized so as to prevent passage of the head member of the tack into the lumen,
wherein the sleeve includes a rigid portion and a collapsible portion, the collapsible portion being configured to collapse along a line substantially parallel to the longitudinal axis of the sleeve to thereby shorten the sleeve; and
a handle coupled to the sleeve, wherein the handle has a longitudinal axis that is transverse to the longitudinal axis of the sleeve.

18. The device of claim 17, wherein the handle includes two opposing members on opposite sides of the longitudinal axis of the handle, the opposing members being biased apart from one another to form an opening between the opposing members in the absence of an overriding force.

19. The device of claim 18, wherein the handle is coupled to the sleeve such that after the device is actuated to cause the collapsible portion to collapse, the opposing members of the handle bias the collapsible portion of the sleeve toward an uncollapsed position.

20. A method of puncturing bone to provide an access point for intraosseous delivery of a medicament, the method comprising:
    providing a puncture device, the puncture device including
        a tack having a flattened head member and an elongate member extending from the head member;
        a sleeve having a proximal end, a distal end, and a lumen extending along a longitudinal axis between the proximal end and the distal end, the lumen being sized so as to receive the elongate member of the tack and being sized so as to prevent passage of the head member of the tack into the lumen,
        wherein the sleeve includes a rigid portion and a collapsible portion, the collapsible portion being configured to collapse along a line substantially parallel to the longitudinal axis of the sleeve to thereby shorten the sleeve; and
        a handle coupled to the rigid portion of the sleeve;
    positioning the distal end of the sleeve at a targeted area adjacent to a targeted tooth to be anesthetized; and
    actuating the puncture device to cause the elongate member of the tack to pass into and through cortical bone at the targeted area.

* * * * *